(12) United States Patent
Jain

(10) Patent No.: US 9,974,489 B2
(45) Date of Patent: May 22, 2018

(54) MONITORING DEVICE AND SYSTEM FOR PROVIDING AN ALERT WHEN AN INFANT IS UNRESPONSIVE TO STIMULUS

(71) Applicant: Circus World Displays Ltd., Niagara Falls (CA)

(72) Inventor: Rajesh Jain, Virgil (CA)

(73) Assignee: CIRCUS WORLD DISPLAYS LTD., Niagara Falls, Ontario ( * ) Notice: Subject to any disclaimer, the term of this patent is extended or adjusted under 35 U.S.C. 154(b) by 239 days.

(21) Appl. No.: 14/726,801

(22) Filed: Jun. 1, 2015

(65) Prior Publication Data
US 2016/0345914 A1    Dec. 1, 2016

(51) Int. Cl.
*A61B 5/00*    (2006.01)
*A61B 5/11*    (2006.01)
(Continued)

(52) U.S. Cl.
CPC .......... *A61B 5/7282* (2013.01); *A61B 5/0077* (2013.01); *A61B 5/1118* (2013.01); *A61B 5/1123* (2013.01); *A61B 5/4884* (2013.01); *A61B 5/747* (2013.01); *A61B 7/00* (2013.01); *A61B 5/0022* (2013.01); *A61B 5/0205* (2013.01); *A61B 5/6804* (2013.01); *A61B 5/6808* (2013.01); *A61B 5/746* (2013.01); *A61B 2503/04* (2013.01); *A61B 2560/0242* (2013.01); *A61B 2562/0219* (2013.01)

(58) Field of Classification Search
CPC ......... A61B 5/11; A61B 5/113; A61B 5/1135; A61B 5/1116; A61B 5/1118; A61B 5/742; A61B 5/746; A61B 5/0205; A61B 5/6804; A61B 2562/0204; A61B 2562/0219; A61B 2503/04; A61B 5/0077; A61B 5/1123; A61B 5/4884; A61B 5/747; A61B 5/7282; G08B 21/02; G08B 21/0202

See application file for complete search history.

(56) References Cited

U.S. PATENT DOCUMENTS 5,515,865 A    5/1996  Scanlon
6,266,558 B1 *  7/2001  Gozani .............. A61B 5/04001
                                              600/547

(Continued)

OTHER PUBLICATIONS

International Search Report and Written Opinion for International Application Serial No. PCT/IB2016/000826, dated Sep. 27, 2016, 8 pages.

(Continued)

*Primary Examiner* — Max Hindenburg
(74) *Attorney, Agent, or Firm* — Amin, Turocy & Watson, LLP

(57) ABSTRACT

Described is an infant monitoring and alerting system capable of determining an absence of movement by an infant. When an absence of movement is detected the monitor attempts to stimulate movement using stimuli that may include a vibration, an audible alert, or a visual alert. If no movement is detected in response to the stimuli, the monitor may provide another instance of stimuli which may include stimuli at an elevated intensity or additional and/or different stimuli. The additional instance of stimuli may further attempt to stimulate movement by the infant and may also function as an alert to the caregiver that their attention may be required.

20 Claims, 7 Drawing Sheets

(51) Int. Cl.
*A61B 7/00* (2006.01)
*A61B 5/0205* (2006.01)

(56) References Cited

U.S. PATENT DOCUMENTS

| | | |
|---|---|---|
| 6,765,489 B1 | 7/2004 | Ketelhohn |
| 7,009,520 B2 | 3/2006 | Thompson |
| 7,250,846 B2 | 7/2007 | Ebling et al. |
| 8,094,013 B1 | 1/2012 | Lee et al. |
| 8,461,996 B2 | 6/2013 | Gallagher |
| 8,864,665 B2 | 10/2014 | Rotondo et al. |
| 8,866,621 B2 | 10/2014 | Wolfe et al. |
| 2006/0097879 A1 | 5/2006 | Lippincott |
| 2011/0221598 A1 | 9/2011 | Eschler et al. |
| 2012/0299732 A1 | 11/2012 | Vogel |
| 2015/0009029 A1 | 1/2015 | Martin |

OTHER PUBLICATIONS

Office Action for U.S. Appl. No. 14/872,644 dated Jul. 3, 2017, 21 pages.

\* cited by examiner

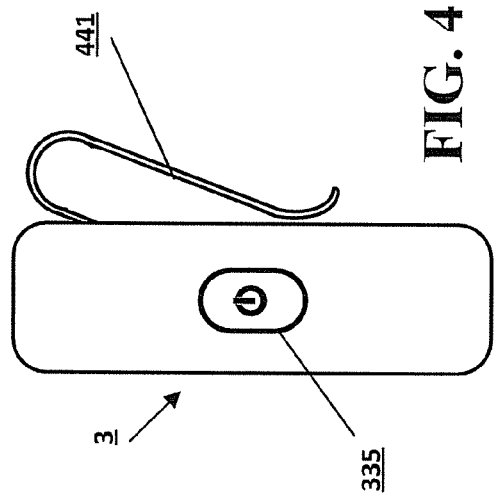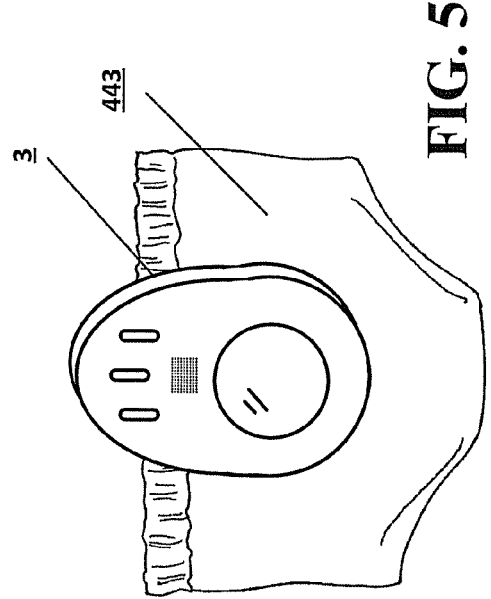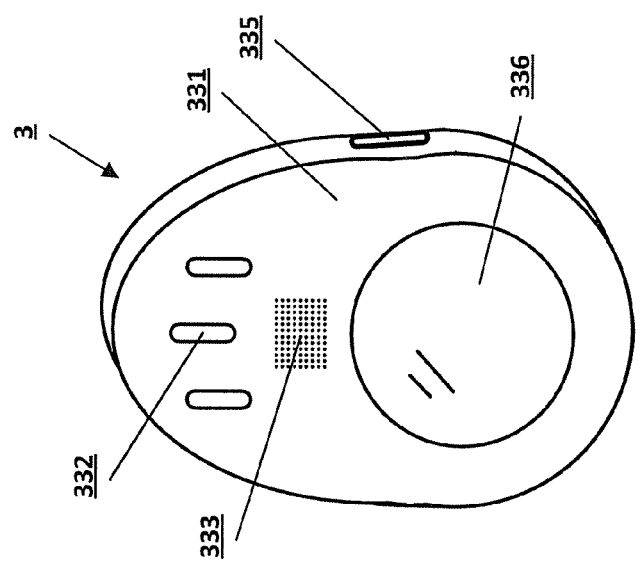

MONITORING DEVICE AND SYSTEM FOR PROVIDING AN ALERT WHEN AN INFANT IS UNRESPONSIVE TO STIMULUS

BACKGROUND

Systems that monitor infants are becoming increasingly popular, and these systems generally comprise a monitor unit that is placed close to an infant, and a remote unit that communicates with the monitor unit to provide a caregiver with information. For example, the most common monitoring systems have a microphone in the monitor unit for capturing sounds, and these sounds are sent to the remote unit where they are broadcast to the caregiver. Unfortunately, these systems typically only provide the caregiver with audio information. If a caregiver does not hear anything that would indicate distress (e.g. crying), it is often assumed that the infant is safe and soundly sleeping. There may be instances, however, where the infant is in distress without making any sound. Accordingly, receiving audio information alone may not always be the most effective technique for reassuring caregivers.

BRIEF SUMMARY

In an implementation, described is a monitoring device attachable to an infant. The monitoring device may include an accelerometer configured to detect movement information of the infant and one or more stimulus generating components configured to generate stimuli. The stimuli may include at least one of a vibration stimulus, an audible stimulus, and a visual stimulus. The monitoring device may include a controller configured to determine, based on the movement information, an absence of movement by the infant for a predetermined period of time and initiate, in response to the determined absence of movement, a first instance of the stimuli to stimulate a responsive movement by the infant. The controller may also be configured to determine, based on the movement information following the first instance of the stimuli, a continued absence of movement by the infant and initiate, in response to the determined continued absence of movement, a second instance of the stimuli to further stimulate the responsive movement by the infant and to alert a caregiver that the infant is unresponsive.

In another implementation, described is an infant monitoring system. The system may include a monitoring device, a transmitting device, and a receiving device. The monitoring device may be attachable to the infant and may include an accelerometer configured to detect movement information of the infant and one or more stimulus generating components configured to generate stimuli. The stimuli may include at least one of a vibration stimulus, an audible stimulus, and a visual stimulus. The monitoring device may include a controller configured to determine, based on the movement information, an absence of movement by the infant for a predetermined period of time and initiate, in response to the determined absence of movement, a first instance of the stimuli to stimulate a responsive movement by the infant. The controller may also be configured to determine, based on the movement information following the first instance of the stimuli, a continued absence of movement by the infant and initiate, in response to the determined continued absence of movement, a second instance of the stimuli to further stimulate the responsive movement by the infant and to alert a caregiver that the infant is unresponsive.

The transmitting device may be placed within a vicinity of the monitoring device and may include a microphone configured to capture audio and a transmitter configured to transmit information to a receiving device. The transmitted information may include information based on the captured audio.

The receiving device may be placed within a vicinity of the caregiver and may include a receiver configured to receive the transmitted information from the transmitting device and one or more output components configured to produce output based on the received information, and in some cases, an alert may be outputted.

In yet another implementation, described is a monitoring device attachable to an infant. The monitoring device may include an accelerometer configured to detect movement information of the infant and one or more stimulus generating components configured to generate stimuli. The stimuli may include at least one of a vibration stimulus, an audible stimulus, and a visual stimulus. The monitoring device may include a controller configured to determine, based on the movement information, an absence of movement by the infant for a predetermined period of time and initiate, in response to the determined absence of movement, a first instance of the stimuli to stimulate a responsive movement by the infant. The controller may also be configured to determine, based on the movement information following the first instance of the stimuli, a continued absence of movement by the infant and initiate, in response to the determined continued absence of movement, a second instance of the stimuli that elevates an intensity of one or more stimuli included in the first instance of the stimuli.

In yet another implementation, described is a method of monitoring an infant with a monitoring device attachable to an infant and comprising an accelerometer, one or more stimulus generating components, and a controller. The method may include detecting, by the accelerometer, movement information of the infant. The method may also include determining, based on the detected movement information, an absence of movement by the infant for a predetermined period of time and generating, with the one or more stimulus generating components and in response to the determined absence of movement, a first instance of stimuli to stimulate a responsive movement by the infant. In addition, the method may also include determining, based on the detected movement information following the first instance of stimuli, a continued absence of movement by the infant and generating, with the one or more stimulus generating components and in response to the determined continued absence of movement, a second instance of stimuli to further stimulate the responsive movement by the infant and to alert a caregiver that the infant is unresponsive.

BRIEF DESCRIPTION OF THE DRAWINGS

The accompanying drawings, which are included to provide a further understanding of the disclosed subject matter, are incorporated in and constitute a part of this specification. The drawings also illustrate aspects of the disclosed subject matter and together with the detailed description serve to explain the principles of the disclosed subject matter. No attempt is made to show structural details in more detail than may be necessary for a fundamental understanding of the disclosed subject matter and various ways in which it may be practiced.

FIG. 3 shows a front view of an example monitoring device according to an implementation of the disclosed subject matter.

FIG. 4 shows a side view of the example monitoring device with an attachment clip according to an implementation of the disclosed subject matter.

FIG. 5 shows the example monitoring device attached to a diaper with the attachment clip according to an implementation of the disclosed subject matter.

DETAILED DESCRIPTION

Described is a system for alerting a caregiver to potential distress of the infant based on monitoring the infant's movements. The system may include an infant monitoring device that may alert a caregiver that the infant is unresponsive to attempts to stimulate movement by the infant. By stimulating movement in the infant, the monitor may verify whether the infant is in fact in distress, and may reassure a caregiver by startling or awakening the infant.

When in use, the monitoring device may be attached to an article of clothing such as a diaper of the infant and may employ an accelerometer to detect movements of the infant. If the monitoring device determines there is an absence of movement for a predetermined period of time, the monitoring device may generate one or more stimuli such as a vibration stimulus, an audible stimulus (e.g. beeping sound), or visual stimulus (e.g. flashing lights) to attempt to stimulate movement of the infant. After the initial instance of stimuli, if the monitor determines there is a continued absence of movement, the monitoring device may generate another instance of stimuli. The device may produce another instance of stimuli to further stimulate movement of the infant (e.g. awaken the infant) by elevating the intensity of one or more stimuli or by including different or additional types of stimuli. This additional instance of stimuli may also function as an alert and inform the caregiver that the infant is unresponsive and that their attention may be required.

Accordingly, the monitoring device and system described herein provides the advantage of not only providing an alert based on movements (as opposed to mere sounds), but may also aid in providing a proactive technique in reassuring caregivers by attempting to awaken the infant from a potentially distressed state.

The monitoring device may act as a standalone unit or may be part of a system that includes one or more remote devices. These remote devices may include a transmitting device and a receiving device. Accordingly, the use of a transmitting device provides the advantage of the monitoring device not necessarily requiring a wireless interface. For example, a transmitting device may be placed within a vicinity of the monitoring device (e.g. within the infant's room) and a receiving device may be placed within a vicinity of a caregiver (e.g. caregiver's bedside). The transmitting device may capture information from the infant or monitoring device and wirelessly transmit that information to the receiving device. For example, the transmitting device may capture audio of the monitoring device producing an alert and transmit that information to the receiving device. Accordingly, in such a configuration, an alert may be provided at both the monitoring device and the receiving device thereby improving the probability the alert is perceived by the caregiver.

Figure 1:
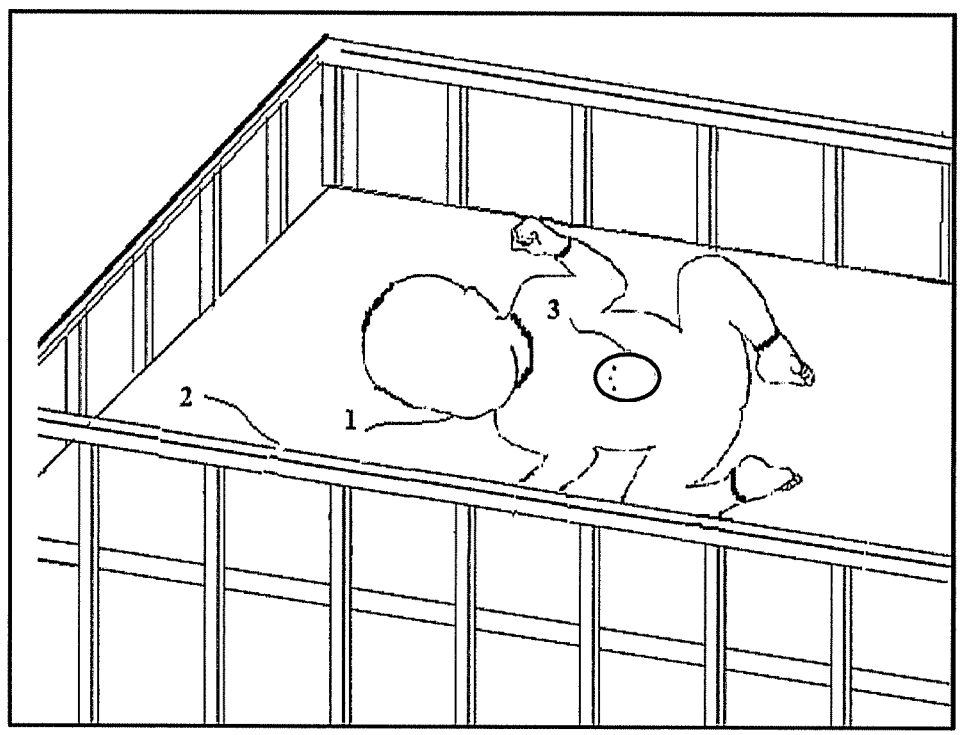
FIG. 1 shows an example of the monitoring device when attached to an infant according to an implementation of the disclosed subject matter.

FIG. 1 shows an example of the monitoring device when attached to an infant according to an implementation of the disclosed subject matter. As shown, the monitoring device 3 may be in physical contact with the infant 1, for example, when the infant 1 is sleeping in a crib 2. As shown in this example, the monitoring device 3 may be attached to an article of clothing of the infant 1. Additionally and as further described herein, the article of clothing may be a diaper to which the monitoring device 3 attaches. Although not shown, the monitoring device 3 may also attach to the infant in different ways and on different parts of the body. For example, the monitoring device 3 may attach to an extremity such as worn around the wrist or ankle, and in such implementations, include appropriate attachment mechanisms (e.g. strap). It should be noted that as referred to herein, attached may include indirect attachment (e.g. to an article of clothing) or direct attachment (e.g. worn around the wrist). In addition, other implementations may include the monitoring device 3 being in physical contact with the infant 1 by being placed, for example, underneath the infant when sleeping.

Figure 2:
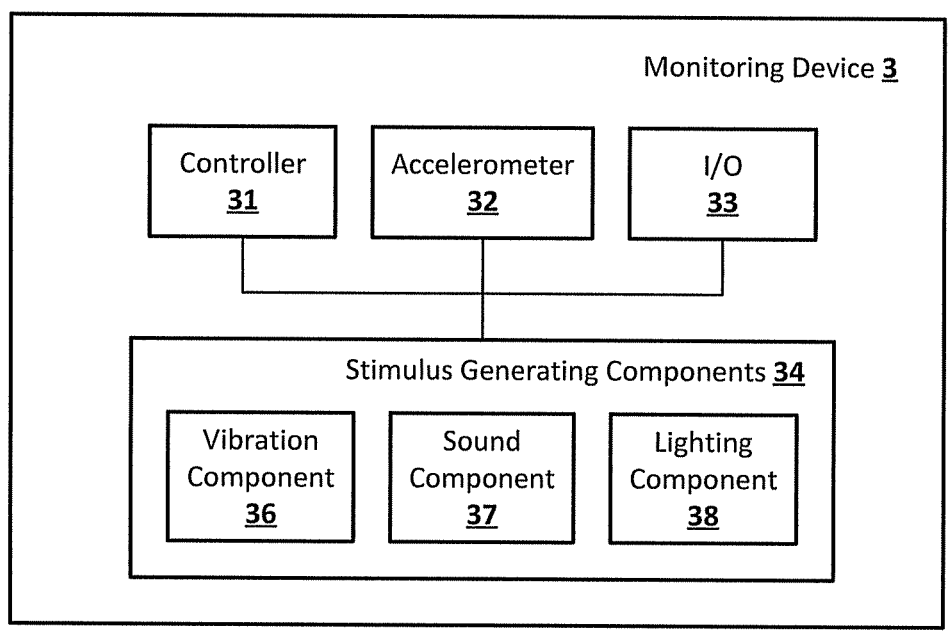
FIG. 2 shows a simplified functional block diagram of a representative monitoring device according to an implementation of the disclosed subject matter.

FIG. 2 shows a simplified functional block diagram of a representative monitoring device according to an implementation of the disclosed subject matter. The monitoring device 3 may include a controller 31, an accelerometer 32, input/output components (I/O) 33, one or more stimulus generating components 34, a power source (not shown), and other components not shown.

The controller 31 may process information and control the functionality of other components of the monitoring device 3 and may include any hardware, software, firmware, or combination thereof. Typically, the controller 31 may be a microcontroller due to its low power consumption, but any other suitable configuration may be used such as a general microprocessor, digital signal processors, FPGAs, ASICs, and the like. The controller 31 may receive signals from the accelerometer 32 and perform functions such as analyzing movement information received from the accelerometer 32 and determine movement characteristics of the infant (e.g. infant 1). The controller 31 may also perform other functions of the monitoring device 3 such as activating one or more of the stimulus generating components 34 and processing functions from the I/O 33. These other functions may include processing inputs to power on/off or activate the device, adjust stimuli settings, etc., and to output information onto a display.

Accelerometer 32 may be any suitable component for detecting movement of the infant. Typically, a tri-axial accelerometer is utilized, but other suitable types and configurations may also be used. Signals produced by the accelerometer 32 may form movement information that is provided to the controller. It should be noted that when analyzing movement information, the controller 31 may distinguish between actual movements attributable to the infant versus movements of the device itself as a result of, for example, generating a vibration.

The accelerometer 32 may be configured to activate upon being attached to the infant. For example, the activation may occur via an explicit input (e.g. a user provides an "activate" input), or activation may occur based on the monitoring device 3 determining the device is actually attached to an infant. The monitoring device 3 may determine that the accelerometer 32 is attached to the infant by employing a sensor (e.g. proximity sensor), or a sensor on an attachment mechanism, or any other suitable technique. As an alternative, or in addition to or in conjunction with the accelerometer 32, the monitoring device 3 may include other sensors such as a heartbeat sensor (e.g. ECG or optical pulse detection) to provide information about the infant's status to the controller 31.

One or more stimulus generating components 34 are configured to generate at least one type of stimuli (or stimulus). The one or more stimulus generating components may include a vibration component 36, a sound component 37, and a lighting component 38 that are configured to generate the at least one vibration stimulus, audible stimulus, and visual stimulus respectively. Depending on the types of stimuli used in an implementation, the device may include the respective stimulus generating components. For example, if a vibration, audible, and visual stimulus is used in an implementation, the monitoring device 3 would include all three components 36, 37, and 38. If only a vibration and audible stimulus are provided, the monitoring device may not necessarily include a lighting component 38. It should be noted that components 36, 37, and 38 may be discrete components or may be part of the same component, and a particular component may be configured to generate more than one type of stimulus.

The vibration component 36 may be any component suitable for generating a vibration stimulus. For example, the vibration component may include a small electric motor with an off-center weight. The vibration stimulus may include a vibration to the monitoring device 3 in a manner such that the vibration is perceptible to the infant, and in some instances, sufficient enough to startle or awaken the infant from a distressed state. The sound component 37 may be any suitable component for producing audible sound. For example, the sound component may include a speaker, or a more rudimentary buzzer or beeper, which may be mechanical, electromechanical, or piezoelectric. The audible stimulus may include an audible alert. Typically, a beep or "alarm" type sound may be used, but other forms of sounds may be used. The lighting component 38 may include any suitable component for providing a visual stimulus. For example, the lighting component 38 may include one or more lights such as LEDs (light-emitting diodes) or a strobe light to create a visual alert such as a flashing light. It should be noted that one or more of the stimulus generating components 34 may be dual (or multiple) purposes components. For example, the lighting component 38 may provide lights that also function as indicators (e.g. power-on) when not producing stimuli. In another example, the sound component 37 may produce sounds to communicate information, such as warning sounds, low battery beeps, power on/off sounds, etc.

I/O 33 (input/output) components may produce various input and output for providing additional functionality to the monitoring device 3. Input components may include, for example, buttons, control knobs, and the like. The I/O 33 may also include interface components for various connectors (e.g. USB, power, etc.). The I/O 33 may also include a display (including a touch-sensitive display) to provide an interface for interacting with the monitoring device 3 (e.g. view device information, adjust settings, etc.).

The monitoring device 3 may also include one or more types of memory (not shown) for storing settings, such as user preferences, and even specific data about the infant, such as movement patterns. The monitoring device 3 may also include a transmitter (not shown) for transmitting information to a remote device (e.g. receiving device as described herein). It should be noted that other components may be part of or connected to the monitoring device 3, and conversely, all of the components shown need not be present.

FIG. 3 shows a front view of an example monitoring device according to an implementation of the disclosed subject matter. As shown, the monitoring device 3 may include an enclosure 331. The enclosure 331 may be any suitable structure capable of protecting and housing the other components in the monitoring device 3. Typically, the enclosure 331 may be formed of plastic, but any other suitable material may be used. In this example, the lighting component (e.g. lighting component 38) includes three LED lights 332. When the LEDs are not activated during a stimulus, the LEDs may convey information. For example, one or more LEDs may indicate a power-on, an activation of monitoring (e.g. indicate the monitor is detecting movements), a low battery indicator, and any other information. The enclosure 331 may also include an aperture 333 for sound from the sound component 37 (e.g. a speaker). As shown in this example implementation, the monitoring device 3 may also include a display 336 to provide an interface for the device. As shown, the monitoring device may also include a power button 335 which may be positioned on the side of the unit.

FIG. 4 shows a side view of the example monitoring device with an attachment clip according to an implementation of the disclosed subject matter. As shown, the monitoring device 3 may include an attachment mechanism. The attachment mechanism may be any suitable mechanism for securing the monitoring device 3 to the infant (directly or indirectly). In this example, a clip 441 may be used to attach the monitoring device 3 to an article of clothing worn by the infant. Typically, the clip 441 may be formed of a durable plastic, but any other suitable material may be used. The clip may also include ridges (not shown) to further grip the article of clothing.

FIG. 5 shows the example monitoring device attached to a diaper with the attachment clip according to an implementation of the disclosed subject matter. As shown in this example, the monitoring device 3 may attach to the waist band of the diaper 443. This allows the monitoring device 3 to remain securely attached to the infant in a non-intrusive manner while still being in physical contact with the infant.

Figure 6:
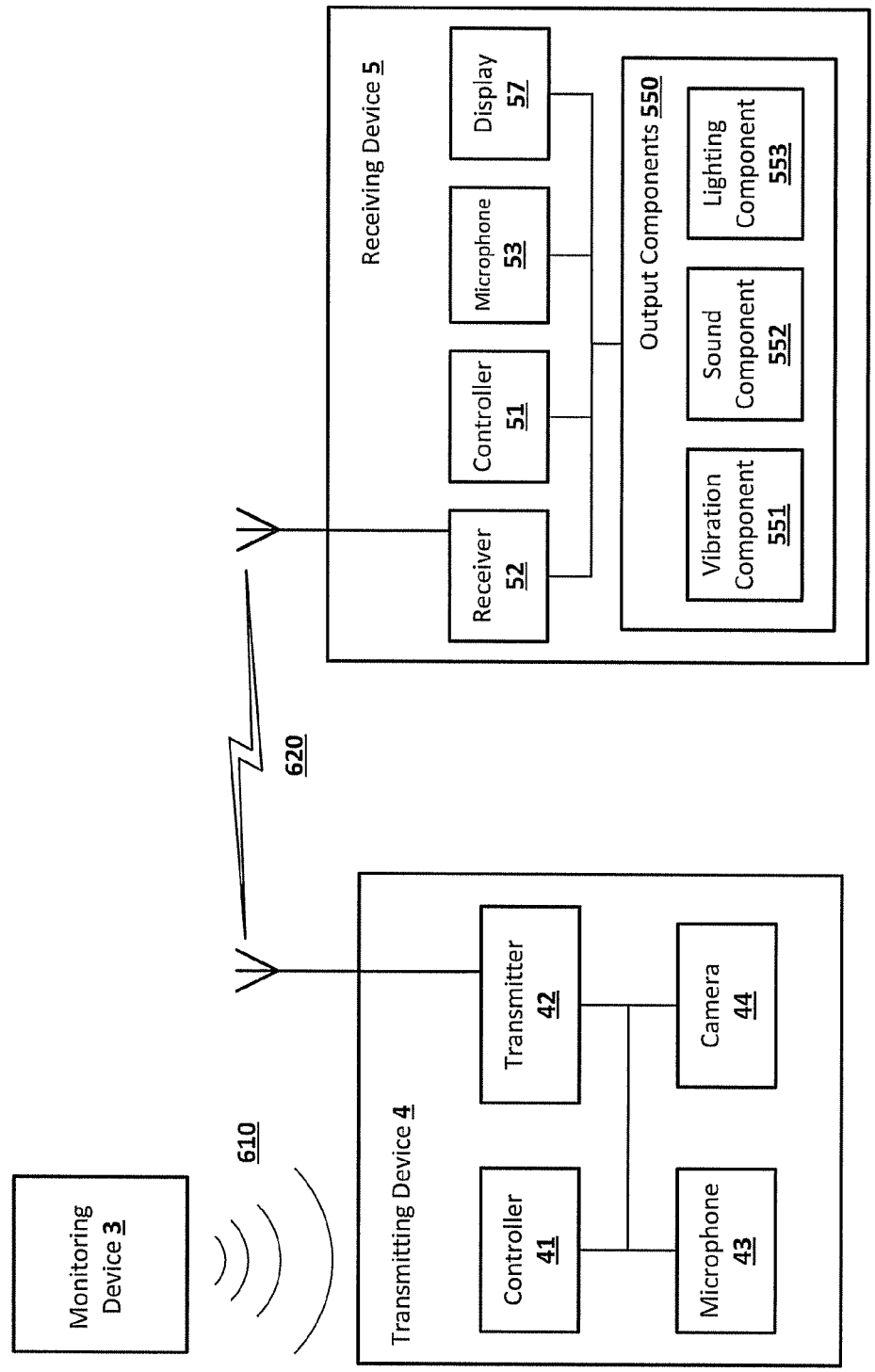
FIG. 6 shows a simplified functional block diagram of a monitoring system including a representative transmitting device and a representative receiving device according to an implementation of the disclosed subject matter.

FIG. 6 shows a simplified functional block diagram of a monitoring system including a representative transmitting device and a representative receiving device according to an implementation of the disclosed subject matter. As shown, the system includes the monitoring device 3 that may emit stimuli 610 (e.g. alert sounds) that may be captured by the transmitting device 4. The transmitting device 4 may then transmit the captured data as information 620 to the receiving device 5. By using a transmitting device 4, information may be transmitted to a device remote from the monitoring device 3 (e.g. receiving device 5) without having the monitoring device 3 employ a wireless interface. Notwithstanding the fact that certain wireless protocols (e.g. low power or near-field communications) may not be harmful to an infant, consumers may still hesitate to utilize a device that emits wireless signals when attached to an infant. Accordingly, the configuration of the system described in this example alleviates such a concern.

The transmitting device may include a controller 41, a transmitter 42, a microphone 43, a camera 44, power source (not shown) and other components not shown. The controller 41 may process information and control the functionality of other components of the transmitting device 3 and may include any hardware, software, firmware, or combination thereof. Typically, the controller 41 may be a microcontroller due to its low power consumption, but any other suitable configuration may be used such as a general microprocessor, digital signal processors, FPGAs, ASICs, and the like.

The microphone 43 may be any suitable type of microphone for capturing audio such as sounds from the infant and/or the monitoring device 3, as well as other ambient noises. The camera 44 may be any suitable type of camera for capturing video such as video of the infant. For example, the camera may be configured to work in low light conditions. In addition, the camera may be configured to be controlled (e.g. repositioned) from a remote device such as from the receiving device 4, a portable remote, or other device such as a smartphone with a specialized application ("app").

The transmitter 42 may be configured to wirelessly transmit information such as multimedia (e.g. audio and/or video) to the receiving device 5. Any suitable wireless protocol may be used including communications through a network (e.g. home network, internet). Typically, in order to conserve battery power and to limit potential wireless radiation, a low power technology may be used. In implementations, the transmitting device 4 may not merely capture/reproduce data in a "pass-through" manner, but may process the captured multimedia to determine that an alert has been activated based on volume, pattern, tone, etc. of the stimuli. Accordingly, a specialized notification may be sent to the receiving device 5 which may in turn generate an alert. As a result, concurrent alerts may be provided at the monitoring device 3 and the receiving device 5 to improve reachability of the alert.

As shown, the system may also include a receiving device 5. The receiving device 5 may be a proprietary component sold, for example, with the monitoring device 3, or may be a general computing device with specialized software (e.g. an installed "app"). For example, the receiving device may be a smartphone, tablet, computer, or the like. The receiving device 5 may include a controller 51, receiver 52, microphone 53, display 57, output components 550, power source (not shown) and other components not shown.

The controller 51 may process information and control the functionality of other components of the receiving device 5 and may include any hardware, software, firmware, or combination thereof. Typically, the controller 51 may be a microcontroller or other suitable configuration may be used as previously described.

The receiver 52 may be configured to receive and process information transmitted by the transmitting device 4. The receiver 52 may be configured to filter out sounds such as sounds above a threshold pitch. This prevents, for example, high pitched noises caused by interference from being outputted by the receiving device 5. Based on the received information, the receiving device may provide output such as reproducing the captured audio and/or providing an alert using the output components 50. In addition, the receiving device 5 may amplify an alert received from transmitting device 4. For example, it may recognize the pattern, or frequency of an alert sound generated by the monitoring device 3.

The output components 550 may include a vibration component 551, a sound component 552, and a light component 553. The respective output components 550 may function in a similar manner as the respective stimulus generating components 34. Accordingly, the descriptions for components 36, 37, and 38 may be referenced with respect to components 551, 552, and 553 respectively. For example, a vibration and an alert sound may be activated by the receiving device 5.

The microphone 53 may be any suitable type of microphone for capturing audio and may be used to determine a level of ambient noise. For example, when the detected ambient noise level of the receiving device 5 exceeds a predefined threshold, the one or more output components 550 may include at least a vibration alert as a local alert. The display 57 may be any suitable display that may act as an interface to the device and may also output video captured by the camera 44 of the transmitting device 4. It should be noted that although a transmitter 42 and receiver 52 are shown, one or both of these components may be part of a transceiver.

Figure 7:
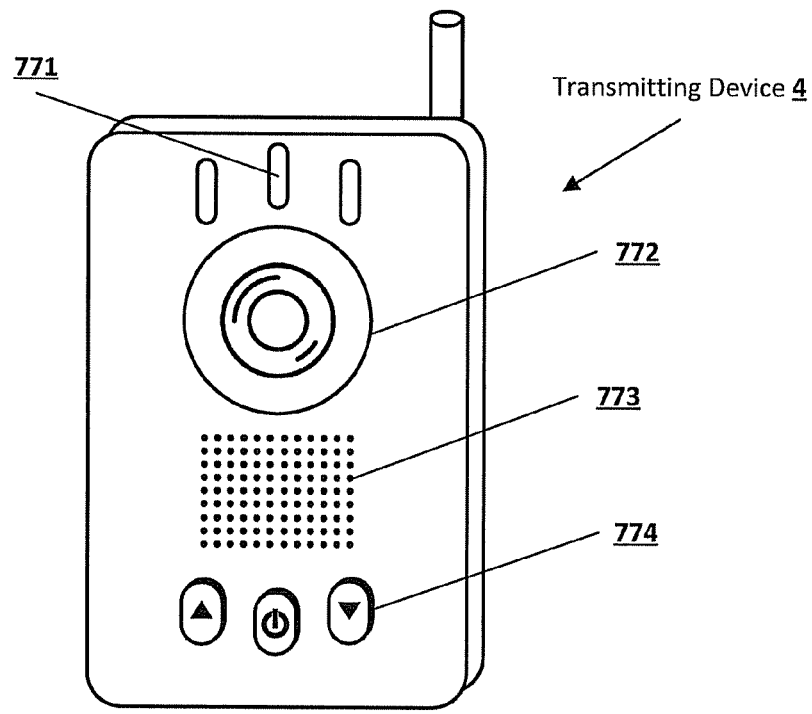
FIG. 7 shows a front view of an example transmitting device according to an implementation of the disclosed subject matter.

FIG. 7 shows a front view of an example transmitting device according to an implementation of the disclosed subject matter. As shown, the transmitting device 4 may include three lights 771 (e.g. indicators), as well as an aperture for a microphone 773. As shown, a camera 772 may be included to capture video. The camera 772 may be configured to be adjusted or repositioned to better focus on an infant. The transmitting device may also include one or more input buttons 774. A shown in this example, the input buttons 774 may include a power button and control buttons (e.g. for camera adjustment, volume, etc.) are shown.

Figure 8:
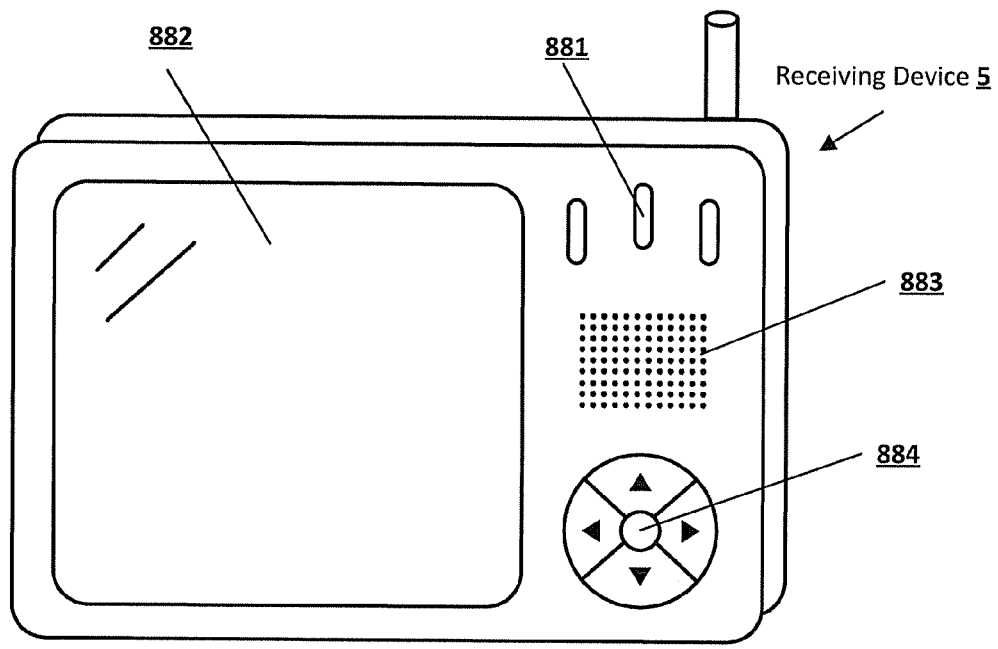
FIG. 8 shows a front view of an example receiving device according to an implementation of the disclosed subject matter.

FIG. 8 shows a front view of an example receiving device according to an implementation of the disclosed subject matter. As shown, the lighting component (e.g. lighting component 553) may include three LED lights 881. These lights may be activated during a visual alert. The transmitting device 5 may also include an aperture 883 for sound that may be generated by the sound component 552 (e.g. a speaker). As shown in this example, the monitoring device 3 may include a display 883 to output captured video and/or provide an interface for the device. In some implementations, the display may include an LCD display, which may be a touch-sensitive display that may acts as an I/O interface. In addition, the receiving device 5 may include input buttons, and in this case control buttons 884. For example, these control buttons 884 may be used to provide, for example, input to the device, navigate an interface, or remotely control the camera 772 of the transmitting device 4. Although a device with a display is shown, the device may also be compact and configured to be placed on the caregiver such as in a pocket.

Figure 9:
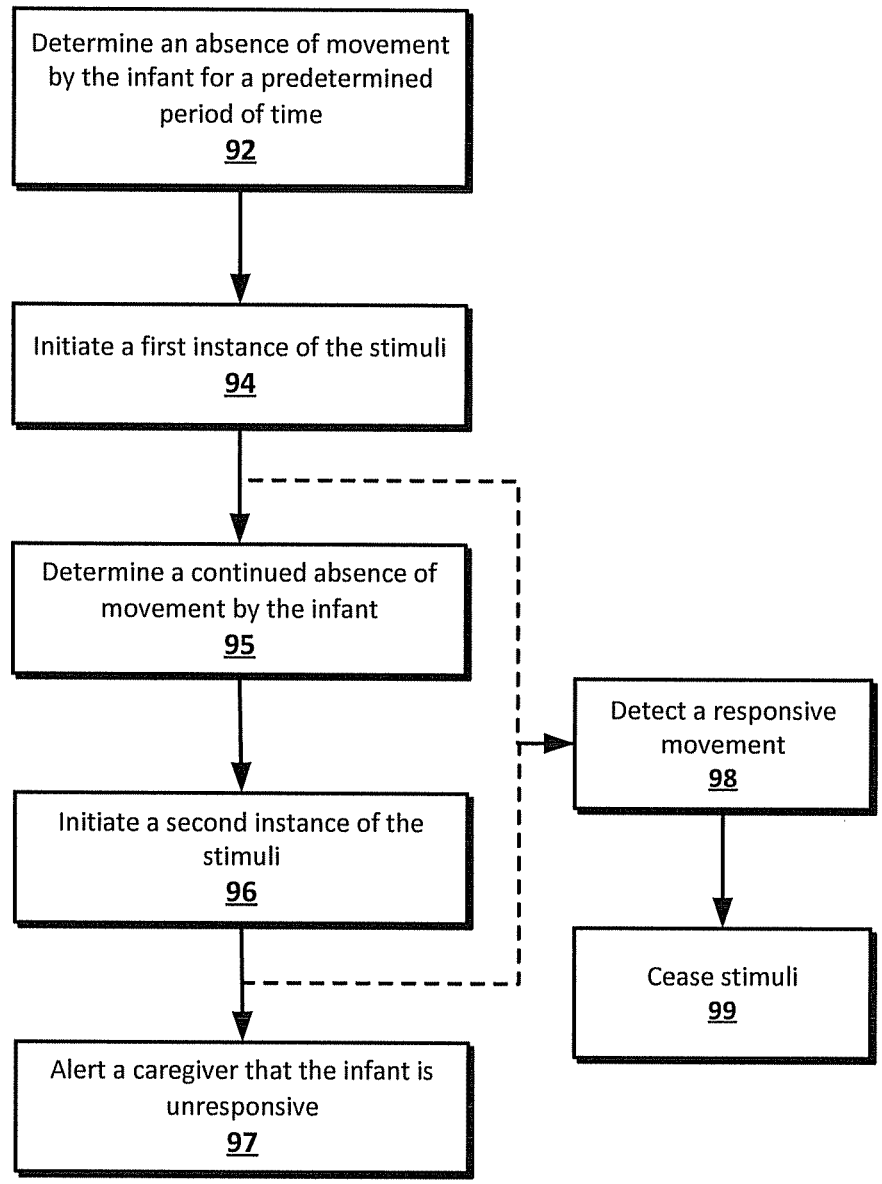
FIG. 9 shows an example flow diagram of the monitoring device in operation according to an implementation of the disclosed subject matter.

FIG. 9 shows an example flow diagram of the monitoring device in operation according to an implementation of the disclosed subject matter. When the monitoring device is attached to the infant, the monitoring device (e.g. through the use of a controller 31) may monitor movements of the infant based on movement information received from an accelerometer (e.g. accelerometer 32). This movement information may provide information regarding the status of the infant. For example, these movements may be associated with abdominal movements, heartbeats, and other general movements such as the infant repositioning and/or shifting during sleep. Accordingly, the monitoring device may extrapolate information from the movement information.

In 92, the monitoring device may determine an absence of movement by the infant for a predetermined period of time based on the movement information. For example, the monitor may recognize abdominal movements, and determine an absence of such movements for a predetermined period of time. The predetermined period of time may be a value set by a manufacturer of the monitoring device (e.g. based on medical information), adjusted by a user, or customized based on attributes of the infant (e.g. weight, age, etc.). For example, the manufacturer may set a default period of time to 10-20 seconds for an absence of movement. In addition, the value may be dynamic and adjusted based on criteria such as learned movement patterns of a particular infant.

In 94, the monitoring device, in response to determining an absence of movement, may initiate a first instance of stimuli. This instance of stimuli may attempt to stimulate a responsive movement by the infant. As described above, an absence (or lack) of movement by the infant may indicate that the infant may potentially be in distressed state. To initiate the stimuli, the monitoring device (e.g. via the controller) may send a signal (i.e. instruction) to the one or more stimulus generating components (e.g. generating components 34) to generate stimuli. As described earlier, the stimuli may include at least one of a vibration stimulus, an audible stimulus, and a visual stimulus. For example, the stimulus may include a vibration, alert sounds (e.g. tone or beep), or lights. The type of stimuli used in an implementation may dictate which types of components are used. As referred to herein, an instance of stimuli may include generating stimuli for a particular duration (e.g. 5 second vibration), continuously (e.g. until a movement is detected), or in a particular pattern. For example, a pattern may include 1 second vibration pulses that occur every other second. In another example, the pattern may include a alert sound every half second or lights that flash at a particular rate. The pattern may continue for a particular duration or may be continuous.

In 95, the monitoring device may determine, based on the movement information following the first instance of the stimuli, a continued absence of movement by the infant. As referred to herein, following an instance of stimuli may include during or upon completion of the stimuli. For example, during a vibration (e.g. a vibration that lasts for 5 seconds), if no movement is detected after a certain period of time (e.g. 3 seconds after commencing the 5 second vibration), the monitor may determine that there is a continued absence of movement. In another example, upon completion of a vibration (e.g. a similar example of a vibration the lasts 5 seconds), if no movement is detected (e.g. at 3 seconds after the completion of the 5 second vibration), the monitoring device may determine that there is a continued absence of movement.

In 96, the monitoring device, in response to determining a continued absence of movement by the infant, may initiate a second instance of stimuli. Based on the lack of a responsive moment (i.e. continued absence of movement), the monitoring device may infer that there is an increased potential for harm to the infant, and thus, an increased urgency to stimulate movement in the infant. Accordingly, in some implementations, the second (or a subsequent) instance of stimuli may function as a way to further stimulate the responsive movement by the infant. For example, the second instance of stimuli may elevate an intensity of one or more stimuli included in the first instance of stimuli. As referred to herein, an elevated intensity may refer to an increase in the degree of stimulus or the rate at which the stimulus is provided. For example, a vibration may be elevated be increasing the force of the vibration. In the instance of an alerting sound, the stimulus may be elevated by increasing the volume of the alert or the rate of the alert (e.g. shorter beep intervals). Similarly, with a flashing light, the brightness of the light may increase or the light my flash at a faster rate. When using a light, the color may also change to indicate an alert. In addition, the second instance of stimuli may elevate the intensity of the one or more stimuli progressively until a predefined maximum intensity is reached or until movement by the infant is detected. For example, if an alerting sound occurs at intervals, each successive sound (e.g. each beep) may increase in volume.

As an alternative, or in addition to, elevating one or more stimuli, the second instance may include at least one additional stimulus not included in the first instance of the stimuli. For example, if the first instance of stimuli includes the vibration stimulus, the second instance of stimuli may include the vibration stimulus and at least one of the audible stimulus and the visual stimulus. In another example, if the first instance of stimuli includes the vibration stimulus and audible stimulus, the second instance of stimuli may include the vibration stimulus, the visual stimulus, and, at an increased volume, the audible stimulus.

In 97, the monitor may alert a caregiver that the infant is unresponsive. In some implementations, the second instance of stimuli may also function as the alert. For example, an audible stimulus (e.g. alert sound) may be included in the second instance of stimuli, which may stimulate the infant and at the same time be of a sufficient volume to alert a caregiver that may not be in the immediate vicinity of the infant (e.g. in another room). In another implementation, the alert may be provided separately from the second instance of stimuli. For example, the second stimuli may further attempt to stimulate movement in the infant (e.g. include a vibration of increased intensity), and if a yet another continued absence of movement is determined, the monitor may provide the alert (e.g. an alert sound) as a third instance of stimuli. In addition, with implementations where the monitoring device includes a transmitter, the alert may include a notification to a remote device (e.g. receiver) that the infant is unresponsive.

During the above operations (e.g. 94-97), the monitor may detect a responsive movement from the infant in 98. As referred to herein, a responsive movement relates to any movement detected after or during an instance of stimuli. For example, a shifting of position after a vibration (whether or not the shift may be directly attributable to the vibration) would constitute a responsive movement. In another example, a responsive movement may include the detection of abdominal movements of the infant.

In 99, the monitor may cease the stimulus in response to the detected movement as described in 98. Ceasing the stimuli may occur while the stimuli are still active. For example, an alert sound or vibration may cease once a movement is detected. In addition, ceasing stimuli may include refraining from producing subsequent patterns of stimuli until a further verification is required (e.g. determining an absence of movement at a later time). For example, if a movement is detected between pulses of vibrations, the monitor will cease generating the pulses.

Figure 10:
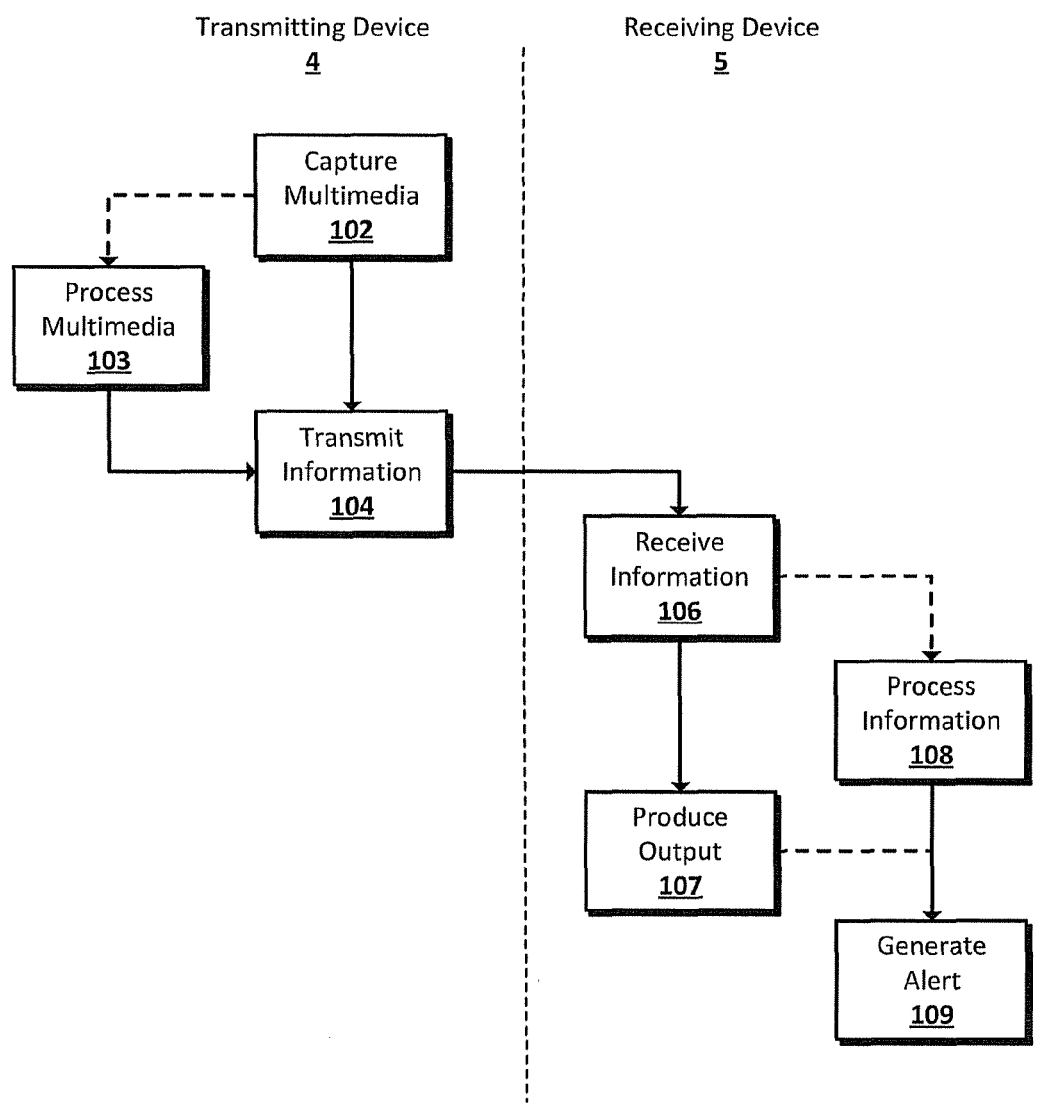
FIG. 10 shows an example flow diagram of the transmitting device and the receiving device in operation according to an implementation of the disclosed subject matter.

FIG. 10 shows an example flow diagram of the transmitting device and the receiving device in operation according to an implementation of the disclosed subject matter. As described earlier, the transmitting device 4 may be placed within a vicinity of the monitoring device (e.g. monitoring device 3). In 102, the transmitting device 4 may capture multimedia. Typically, this includes capturing audio with a microphone (e.g. microphone 43). For example, the audio may include sounds produced by the infant and/or the monitoring device. In some implementations, the multimedia may also include capturing video with a camera (e.g. camera 44). Regardless of the type of multimedia captured, in 104 the transmitting device 4 may transmit the information to a receiving device 5. As described earlier, the receiving device 5 may be placed within a vicinity of the caregiver. In 106, the receiving device 5 may receive the information. In 107, the receiving device 5 may produce output based on the received information. For example, producing output may include reproducing sounds from the infant (e.g. crying) or any alert sounds captured by the transmitting device 4. In another example, producing output may include reproducing video captured by the camera of the receiving device on a display (e.g. display 882).

In addition to capturing/reproducing audio and/or video, the transmitting device 4 or receiving device 5 may recognize that an alert has been generated, and accordingly, the receiving device 5 may generate an alert of its own (e.g. alert local to the caregiver). For example, in 103, the transmitting device 4 may process the captured multimedia and recognize (e.g. via its controller 41), that the captured audio includes sounds associated with an alert sound (e.g. based on volume or pitch). Accordingly, the transmitter 4 as an alternative, or in addition to, sending the captured audio itself, may send as part of the information transmitted to the receiving device 5, a notification (e.g. an instruction) that an alert has been generated. Based on the notification, the receiving device 5 may generate a local alert in 109. In another example, in 108 the receiving device 5 may recognize (via its controller 51) that the received audio information includes audio associated with an alert sound. Accordingly, the receiving device 5 may then generate a local alert. As described earlier, the receiving device 5 may include a vibration component 551, a sound component 552, and a lighting component 553 to generate, based on the received information, a local alert to the caregiver that the infant is unresponsive. The local alert may be generated in a similar manner as described herein with respect to the monitoring device 3 (e.g. instances of stimuli). For example, the receiving device may generate at least one of a vibration, audible alert, and visual alert and various combinations thereof.

It should be noted that although the plural term "stimuli" is used herein, it may be interpreted as "stimuli or stimulus." It should be noted that the disclosure refers to infants, but may be equally applicable to older subjects such as toddlers up to adults and seniors. Moreover, it should be noted that the monitoring device need not be used exclusively as a distress alarm, but may be used purely as a reassurance device. In addition, while the examples provided herein relate to the system being used in a domestic setting, it may also be used in, for example, a clinical or hospital setting. In addition, multiple monitoring devices may communicate with a single receiving (or transmitting) device.

Various implementations described herein may include or be embodied in the form of computer-implemented process and an apparatus for practicing that process. Implementations described herein may also be embodied in the form of a non-transitory computer-readable storage and/or memory containing instructions, wherein, when the instructions are loaded into and executed by a controller (or processor), a device becomes an apparatus for practicing implementations of the disclosed subject matter.

Components such as a controller may be described herein as "configured to" perform various operations or functions. In such contexts, "configured to" includes a broad recitation of structure generally meaning "having circuitry that" performs functions during operation. As such, the component can be configured to perform such functions even when the component is not in a powered-on state.

The flow diagrams described herein are included as examples. There may be variations to these diagrams or the operations (or steps) described therein without departing from the implementations described herein. For instance, the steps may be performed in parallel, simultaneously, a differing order, or steps may be added, deleted, or modified. Similarly, the block diagrams described herein are included as examples. These configurations are not exhaustive of all the components and other arrangements and components may be used without departing from the implementations described herein. For instance, components may be added, deleted, or modified, and may interact in various ways known to an others skilled in the art.

References to "one implementation," "an implementation," "an example implementation," and the like, indicate that the implementation described may include a particular step, feature, structure, or characteristic, but every implementation may not necessarily include the particular step, feature, structure, or characteristic. Moreover, such phrases are not necessarily referring to the same implementation. Further, when a particular step, feature, structure, or characteristic is described in connection with an implementation, such step, feature, structure, or characteristic may be included in other implementations whether or not explicitly described. The term "substantially" may be used herein and may be interpreted as "as nearly as practicable," "within technical limitations," and the like. In addition, the term "or" may be used herein and may be interpreted as "and/or" unless stated otherwise.

The foregoing description, for purpose of explanation, has been described with reference to specific implementations. However, the illustrative discussions above are not intended to be exhaustive or to limit implementations of the disclosed subject matter to the precise forms disclosed. Many modifications and variations are possible in view of the above teachings. The implementations were chosen and described in order to explain the principles of implementations of the disclosed subject matter and their practical applications, to thereby enable others skilled in the art to utilize those implementations as well as various implementations with various modifications as may be suited to the particular use contemplated.

The invention claimed is:

1. A monitoring device attachable to an infant, comprising:
    an accelerometer configured to detect movement information of the infant;
    at least one stimulus generating component configured to generate at least one type of stimulus, wherein the at least one type of stimulus comprises at least one of a vibration stimulus, an audible stimulus, or a visual stimulus; and
    a controller configured to:
        determine a customized period of time for an absence of movement of the infant based on at least one attribute of the infant;
        determine, based on the movement information, the absence of movement by the infant for the customized period of time;

initiate, in response to the determined absence of movement, at least one first stimulus by the at least one stimulus generating component to stimulate a responsive movement by the infant;

determine, based on additional detected movement information by the accelerometer following the at least one first stimulus, a continued absence of movement by the infant; and initiate, in response to the determined continued absence of movement, at least one second stimulus by the at least one stimulus generating component to further stimulate the responsive movement by the infant.

2. The monitoring device of claim 1, wherein the at least one second stimulus comprises a same type of stimulus as the at least one first stimulus, and the at least one second stimulus has a greater intensity of the same type of stimulus than the at least one first stimulus, wherein the at least one second stimulus includes a type of stimulus not included in the at least one first stimulus.

3. The monitoring device of claim 1, wherein the at least one second stimulus includes a type of stimulus not included in the at least one first stimulus.

4. The monitoring device of claim 1, wherein the at least one first stimulus includes the vibration stimulus and the at least one second stimulus includes the vibration stimulus and at least one of the audible stimulus and the visual stimulus.

5. The monitoring device of claim 1, wherein the controller is further configured to cease the at least one first stimulus or the at least one second stimulus upon detection of a movement by the infant.

6. The monitoring device of claim 1, wherein the movement information is associated with abdominal movements of the infant.

7. The monitoring device of claim 1, wherein the monitoring device is attachable to an article of clothing worn by the infant.

8. A monitoring device attachable to an infant, comprising:

an accelerometer configured to detect movement information of the infant;

at least one stimulus generating component configured to generate at least one type of stimulus, wherein the at least one type of stimulus comprises at least one of a vibration stimulus, an audible stimulus, or a visual stimulus; and a controller configured to:
determine a customized period of time for an absence of movement of the infant based on at least one attribute of the infant;
determine, based on the movement information, an absence of movement by the infant for the customized period of time;
initiate, in response to the determined absence of movement, at least one first stimulus by the at least one stimulus generating component to stimulate a responsive movement by the infant;
determine, based on additional detected movement information by the accelerometer following the at least one first stimulus, a continued absence of movement by the infant; and
initiate, in response to the determined continued absence of movement, at least one second stimulus by the at least one stimulus generating component, wherein the at least one second stimulus includes a same type of stimulus as the first stimulus, and the second stimulus has a greater intensity of the same type of stimulus than stimulus.

9. The monitoring device of claim 8, wherein the controller is further configured to alert a caregiver that the infant is unresponsive.

10. The monitoring device of claim 9, wherein the controller is further configured to alert the caregiver as part of the at least one second stimulus.

11. The monitoring device of claim 10, wherein the alert as part of the at least one second stimulus includes at least one of the audible stimulus and the visual stimulus.

12. The monitoring device of claim 8, wherein the at least one first stimulus and the at least one second stimulus includes the vibration stimulus and at least one of the audible stimulus or the visual stimulus, and wherein the intensity of the at least one of the audible stimulus or the visual stimulus is greater in the at least one second stimulus than the at least one first stimulus.

13. The monitoring device of claim 8, wherein the controller is further configured to increase an intensity of the at least one second stimulus progressively until a predefined maximum intensity is reached or until movement by the infant is detected.

14. A method of monitoring an infant with a monitoring device attachable to an infant and comprising an accelerometer, at least one stimulus generating component, and a controller, the method comprising:

determining, by the controller, a customized period of time for an absence of movement of the infant based on at least one attribute of the infant;

detecting, by the accelerometer, movement information of the infant;

determining, based on the detected movement information, the absence of movement by the infant for the customized period of time;

generating, by the at least one stimulus generating component and in response to the determined absence of movement, at least one first stimulus by the at least one stimulus generating component to stimulate a responsive movement by the infant;

determining, based on additional detected movement information by the accelerometer following the at least one first stimulus, a continued absence of movement by the infant; and generating, by the at least one stimulus generating component and in response to the determined continued absence of movement, at least one second stimulus to further stimulate the responsive movement by the infant.

15. The method of claim 14, wherein the at least one second stimulus has a same type of stimulus as the at least one first stimulus, and the at least one second stimulus has a greater intensity of the same type of stimulus than the at least one first stimulus.

16. The method of claim 14, wherein the at least one second stimulus includes a type of stimulus not included in the at least one first stimulus.

17. The method of claim 14, wherein the at least one first stimulus includes the vibration stimulus and the at least one second stimulus includes the vibration stimulus and at least one of the audible stimulus and the visual stimulus.

18. The method of claim 14, further comprising ceasing the at least one first stimulus or the at least one second stimulus upon detection of a movement by the infant.

19. A non-transitory computer-readable medium having instructions stored thereon that, in response to execution, cause a monitoring device attachable to an infant to perform operations comprising:
- determining a customized period of time for an absence of movement of the infant based on at least one attribute of the infant;
- detecting movement information of the infant;
- determining, based on the detected movement information, the absence of movement by the infant for the customized period of time;
- generating, by at least one stimulus generating component of the monitoring device and in response to the determined absence of movement, at least one first stimulus by the at least one stimulus generating component to stimulate a responsive movement by the infant;
- determining, based on additional detected movement information by the accelerometer following the at least one first stimulus, a continued absence of movement by the infant; and
- generating, by the at least one stimulus generating component and in response to the determined continued absence of movement, at least one second stimulus to further stimulate the responsive movement by the infant, wherein the at least one second stimulus includes a type of stimulus not included in the at least one first stimulus.

20. The monitoring device of claim 1, wherein the at least one attribute of the infant comprises a weight of the infant, an age of the infant, or a learned movement pattern of the infant.

* * * * *